United States Patent [19]

Scott et al.

[11] Patent Number: 5,334,196

[45] Date of Patent: Aug. 2, 1994

[54] ENDOSCOPIC FASTENER REMOVER

[75] Inventors: Ian M. Scott, Ridgefield; David A. Nicholas, Trumbull, both of Conn.

[73] Assignee: United States Surgical Corporation, Norwalk, Conn.

[21] Appl. No.: 956,714

[22] Filed: Oct. 5, 1992

[51] Int. Cl.⁵ ............................................. A61B 17/00
[52] U.S. Cl. .................................... 606/138; 254/28
[58] Field of Search ........ 606/138, 139, 142, 170–172, 606/187; 254/28

[56]  References Cited

U.S. PATENT DOCUMENTS

| | | | |
|---|---|---|---|
| 4,226,239 | 10/1980 | Polk et al. | 606/141 |
| 4,434,796 | 3/1984 | Karapetian et al. | 606/220 |
| 4,487,394 | 12/1984 | Rothfuss et al. | 254/28 |
| 4,589,631 | 5/1986 | Marcus | 254/28 |
| 4,637,538 | 1/1987 | Wagner | 254/28 |
| 4,802,478 | 2/1989 | Powell | 606/138 |
| 4,805,876 | 2/1989 | Blake et al. | 254/28 |
| 5,015,250 | 5/1991 | Foster | 606/147 |
| 5,035,400 | 7/1991 | Altenbach, Jr. | 254/28 |
| 5,049,153 | 9/1991 | Nakao et al. | 606/138 |
| 5,085,661 | 2/1992 | Moss | 606/139 |
| 5,156,608 | 10/1992 | Troidl et al. | 606/142 |

FOREIGN PATENT DOCUMENTS

| | | | |
|---|---|---|---|
| 3301803 | 6/1984 | Fed. Rep. of Germany | 606/138 |
| 4115937 | 7/1992 | Fed. Rep. of Germany . | |

OTHER PUBLICATIONS

Ethicon Endo-Surgery; Feb. 24, 1992 Hospital Price List.

*Primary Examiner*—Stephen C. Pellegrino
*Assistant Examiner*—Gary Jackson

[57]   ABSTRACT

A surgical apparatus for removing fasteners from the body includes an endoscopic portion for insertion through an endoscopic tube and a fastener removing assembly positioned at the distal end of the endoscopic portion. By engaging a fastener with the fastener removing assembly, a surgeon can actuate the assembly and cause the fastener to distort to a configuration suitable for removal from the body.

26 Claims, 10 Drawing Sheets

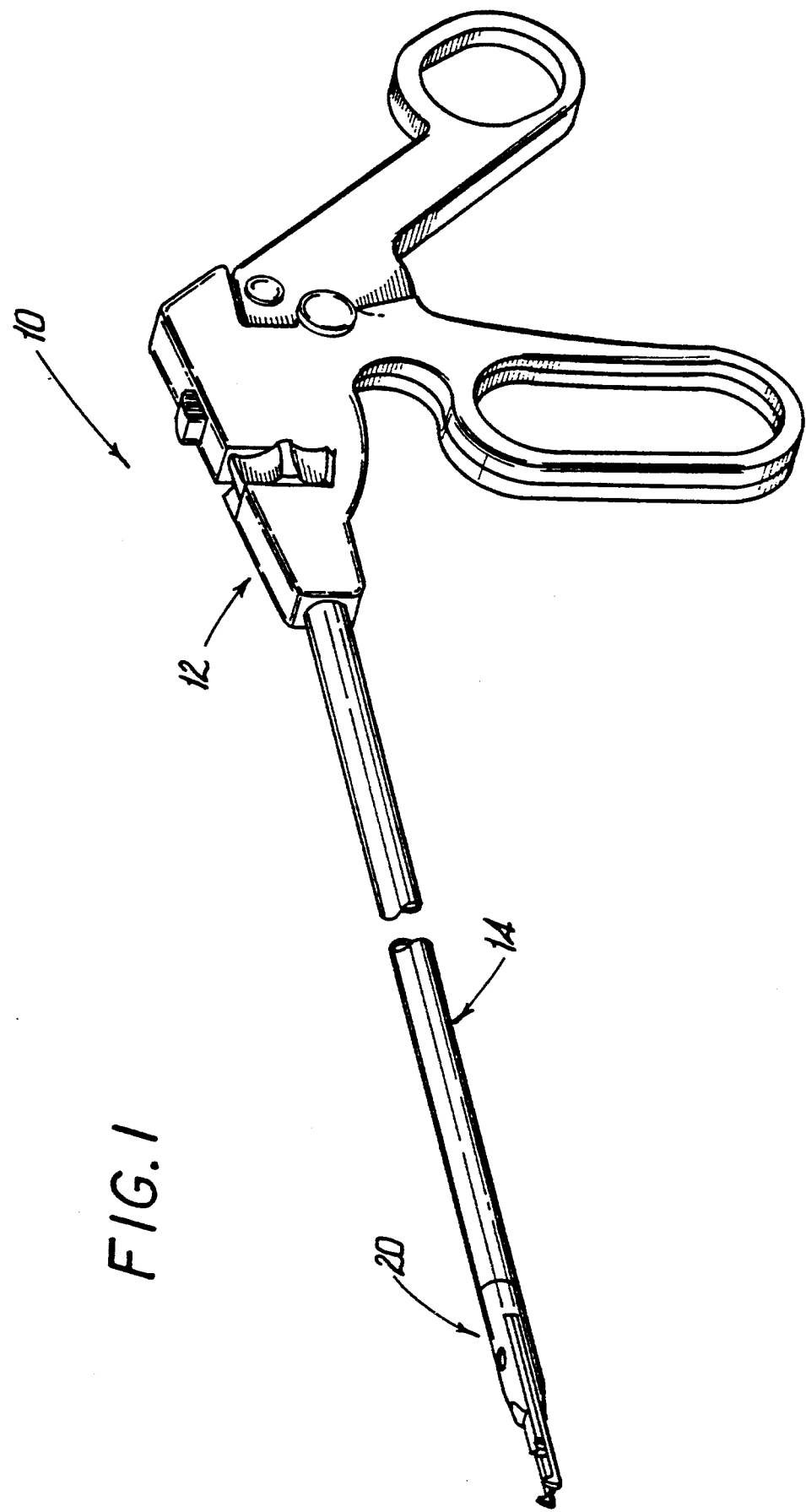

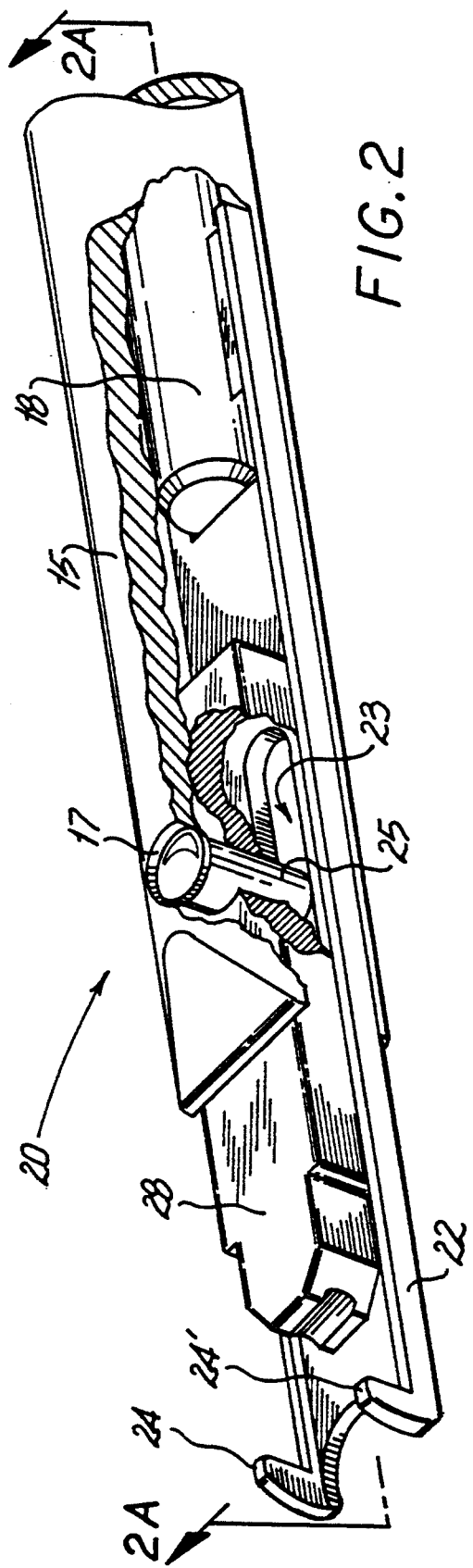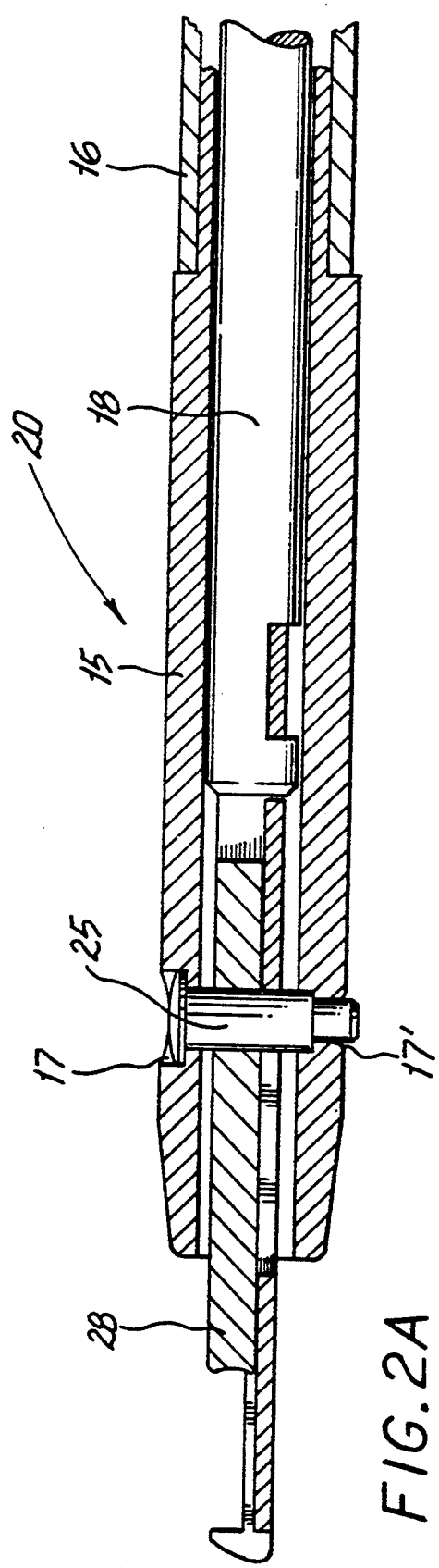

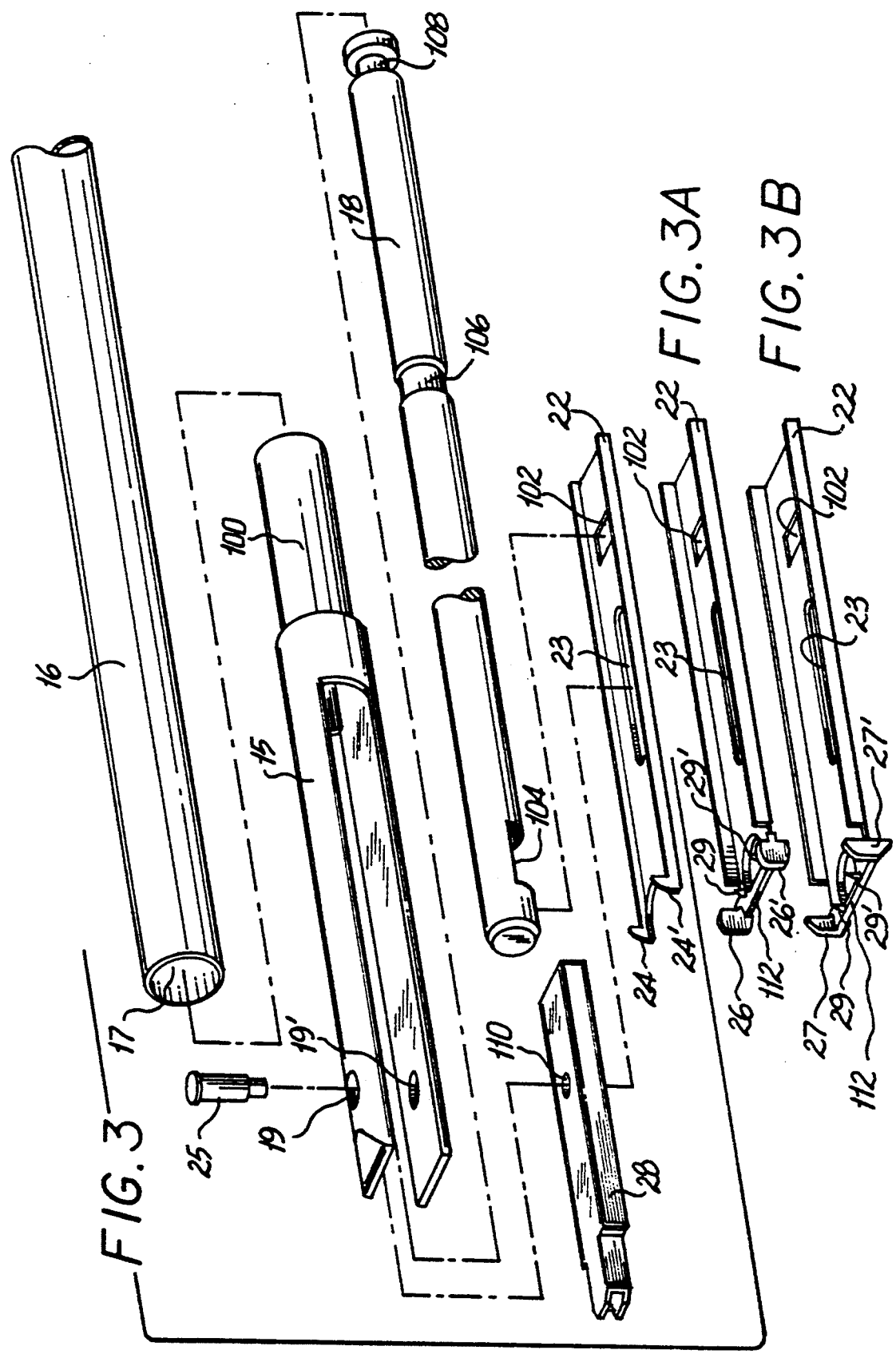

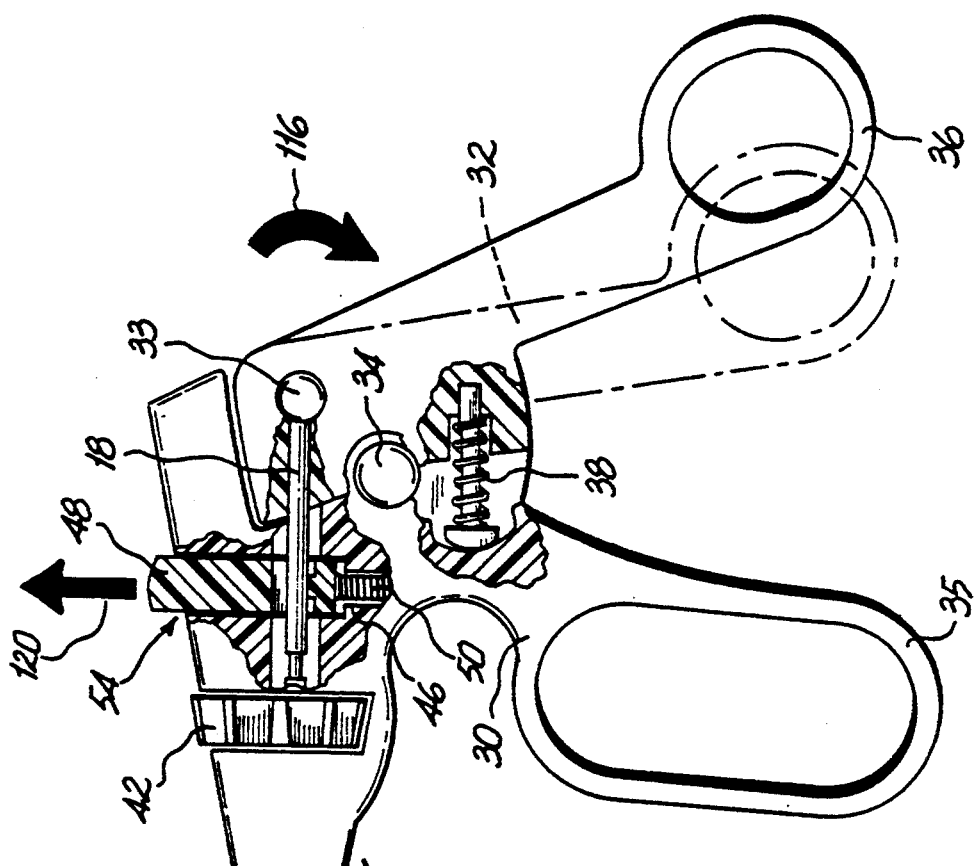
FIG. 4
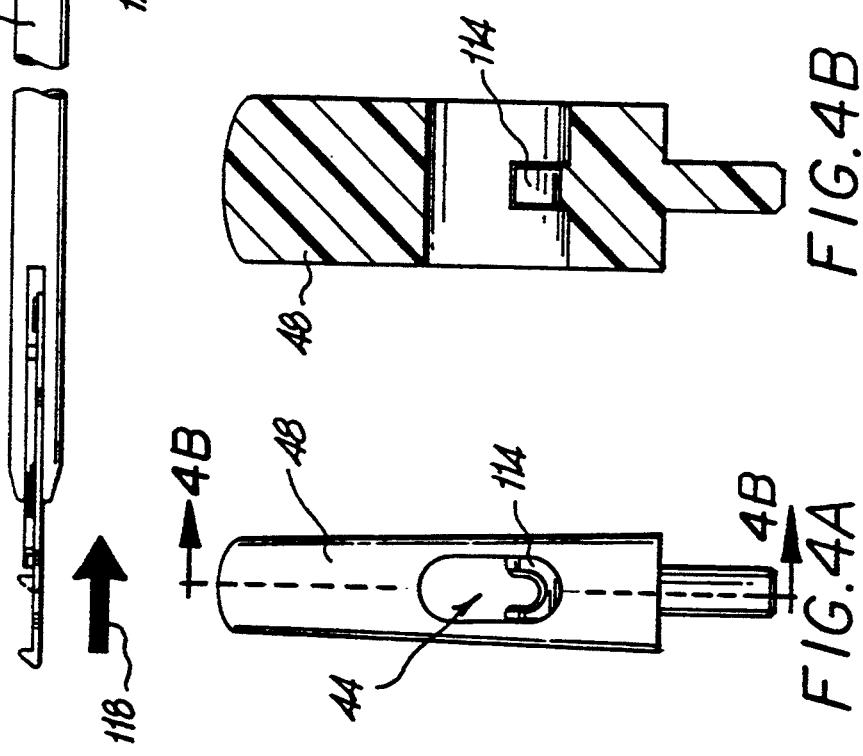
FIG. 4A
FIG. 4B

ENDOSCOPIC FASTENER REMOVER

BACKGROUND OF THE INVENTION

1. Field of the Invention

The present invention relates to surgical fastener removers, and more particularly relates to surgical fastener removers for use in endoscopic and laparoscopic procedures.

2. Discussion of the Prior Art

Laparoscopic and endoscopic surgical procedures are minimally invasive procedures in which operations are carried out within the body by means of elongated instruments inserted through small entrance openings in the body. The initial opening in the body tissue to allow passage of the endoscopic or laparoscopic instruments to the interior of the body may be a natural passageway of the body, or it can be created by a tissue piercing instrument such as a trocar. With the aid of a cannula assembly inserted into the opening, laparoscopic or endoscopic instrumentation may then be used to perform desired surgical procedures.

Laparoscopic and endoscopic surgical procedures generally require that any instrumentation inserted in the body be sealed, i.e. provisions must be made to ensure that gases do not enter or exit the body through the instrument or the entrance incision so that the surgical region of the body, e.g. the peritoneum, may be insufflated. Mechanical actuation of such instruments is for the most part constrained to the movement of the various components along a longitudinal axis with means provided to convert longitudinal movement to lateral movement where necessary. Because the endoscopic or laparoscopic tubes, instrumentation, and any required punctures or incisions are relatively narrow, endoscopic or laparoscopic surgery is less invasive and causes much less trauma to the patient as compared to procedures in which the surgeon is required to cut open large areas of body tissue.

Surgical fasteners or staples are often used to join body tissue during laparoscopic and endoscopic procedures. Such fasteners typically have a pair of legs joined by a backspan and are set into the body by means of an elongated instrument which crimps the fastener legs to secure the fastener and tissue. Once a fastener is crimped into place, it may be necessary to remove the fastener. This need can arise when a fastener is misplaced or otherwise determined to be in an undesirable location. However, it is extremely difficult to remove the fastener without causing damage to the surrounding tissue, especially due to the nature of minimally invasive surgery wherein the fastener must be manipulated from a position outside the body.

Various types of surgical fastener or staple removers are known but are not suited for endoscopic procedures. For example, U.S. Pat. No. 4,589,631 discloses a surgical staple remover comprising two pivotally connected arms, each of which is made up of a proximal handle and a distal nose piece. The apparatus operates in a manner similar to a pair of pliers- the surgeon grasps a staple backspan with the nose piece of the remover and then squeezes the handles to bend the staple's backspan to cause the staple legs to pull out of the body. In operation, however, such surgical fastener removers are not suited for endoscopic or laparoscopic surgery because they cannot be inserted into a cannula assembly.

Therefore, the novel surgical apparatus pursuant to the present invention advantageously provides an endoscopic surgical fastener remover configured and dimensioned to be fully operational within a finite space, such as in an abdominal cavity and a cannula assembly, to remover fasteners which have been applied endoscopically.

SUMMARY OF THE INVENTION

The present invention provides a novel endoscopic or laparoscopic surgical apparatus which is a lightweight, easy to use and may be operated with one hand. The apparatus comprises an endoscopic portion having fastener removing means positioned at the distal end and fastener removing actuating means positioned remote from the fastener removing means.

The endoscopic portion may further comprise an outer tube, configured and dimensioned to be inserted through a cannula, and an inner rod slidably disposed therein. The fastener removing means comprises a stationary member and a movable member disposed within a distal nose piece. The inner rod is connected at a distal end to the movable member of the fastener removing means and at its proximal end to the fastener removing actuating means. The actuating means comprises a handle assembly wherein there is at least one stationary handle and at least one pivotable handle. With the inner rod connected to a pivotable handle, manipulation of the pivotable handle causes the inner rod to slide axially within the outer tube. This provides means for controlled movement of the movable member of the fastener removing means and enables the surgeon to remove fasteners from the body. The outer tube and inner rod of the endoscopic portion can be rotatably connected to the handle assembly, advantageously allowing the surgeon to rotate the fastener removing means to a desired orientation without rotating the entire handle assembly. The present invention may also include a locking mechanism disposed within the handle assembly in order to secure the inner rod, and therefore the movable member of the fastener removing means, in a fixed position relative to the outer tube.

In operation, a surgeon can rotate the endoscopic portion and fastener removing means to align the removing means with the backspan of a fastener. Once aligned, the apparatus can be maneuvered to cause the backspan to become located between the movable and stationary members of the fastener removing means. By pivoting the pivotable handle, the surgeon can then cause the inner rod and, therefore, the movable member of the fastener removing means, to slide axially. Axial movement of the movable member towards the stationary member of the fastener removing means will cause the fastener to become pressed therebetween. Further movement of the pivotable handle, inner rod, and movable member of the fastener removing means causes the fastener to distort to a configuration suitable for removal. An optional locking mechanism disposed within the handle assembly can provide means to ensure that the movable and stationary members of the fastener removing means do not move relative to each other while the uncrimped fastener is being removed, thus preventing an undesired release of the fastener into the body cavity.

BRIEF DESCRIPTION OF THE DRAWINGS

The foregoing objects and other features of the invention will become more readily apparent and may be understood by referring to the following detailed description of illustrative embodiments of the endoscopic or laparoscopic surgical apparatus for removing fasteners, taken in conjunction with the accompanying drawings, in which:

FIG. 1 illustrates a perspective view of a first embodiment of an endoscopic or laparoscopic surgical apparatus of the present invention;

FIG. 2 illustrates a side plan cut-away view of the fastener removing portion of the apparatus;

FIG. 2A is cross sectional view taken along lines 2A—2A of FIG. 2;

FIG. 3 illustrates an exploded perspective view of the endoscopic and fastener remaining portions of the apparatus of FIG. 1;

FIGS. 3A and 3B illustrate alternate embodiments of the forked portions of the fastener removing means;

FIG. 4 illustrates a side plan cut-away view of the handle assembly depicting the movement of the pivotable handle from the open to the closed position;

FIG. 4A illustrates a front view of the latching mechanism of FIG. 4;

FIG. 4B is a cross sectional view taken along lines 4B—4B of FIG. 4A;

FIG. 6A illustrates the apparatus engaging a fastener prior to distortion of the fastener.

FIG. 6B illustrates a fastener after being deformed by the apparatus.

DETAILED DESCRIPTION OF THE PREFERRED EMBODIMENTS

Figure 5:
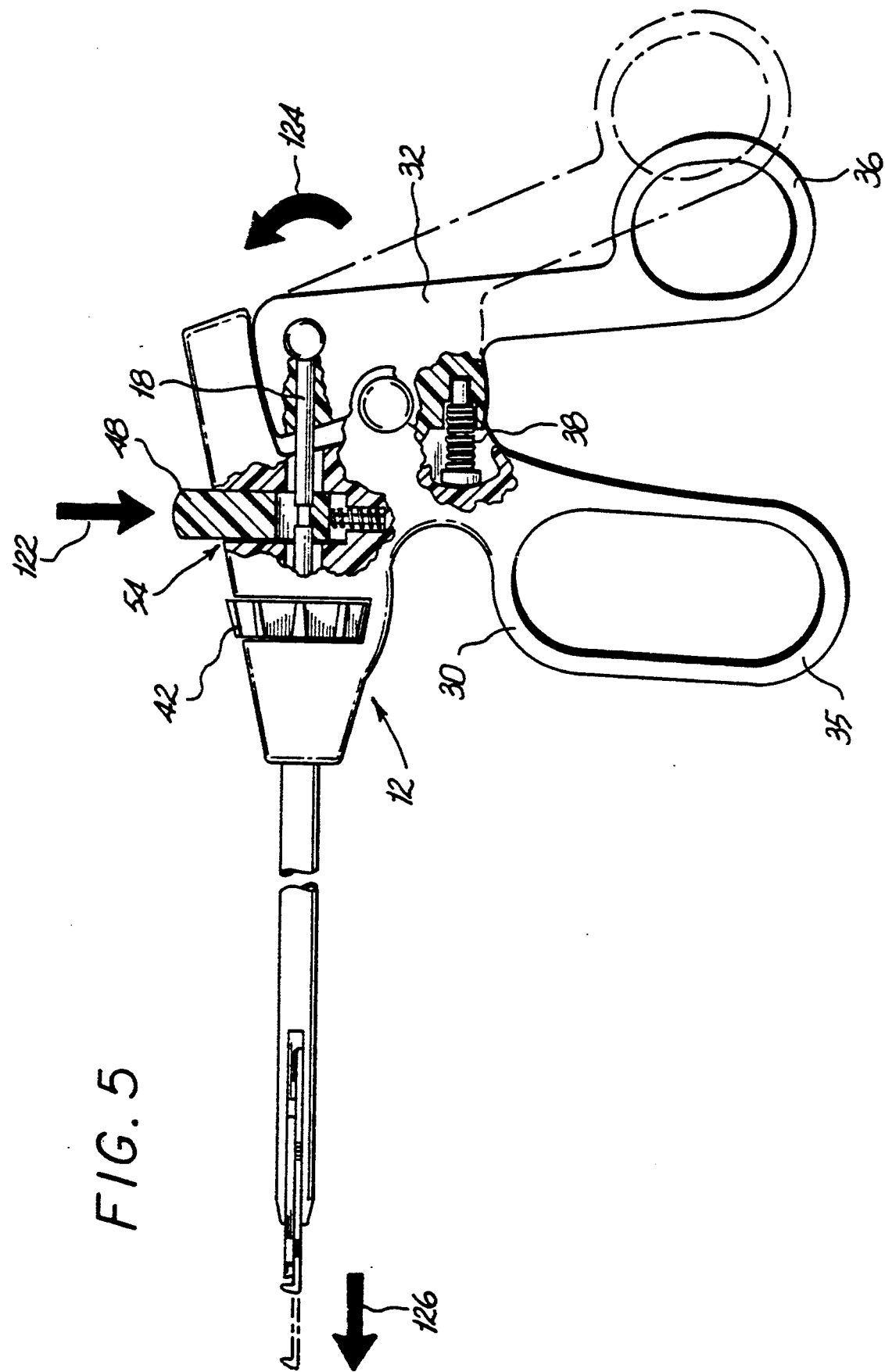
FIG. 5 illustrates a side plan cut-away view of the handle assembly, depicting the movement of the pivotable handle from a closed position to an open position.

Referring now in specific detail to the drawings, in which like reference numerals identify similar or identical elements, FIG. 1 illustrates a first embodiment of the endoscopic or laparoscopic surgical apparatus 10 for removing surgical fasteners. Apparatus 10 comprises endoscopic portion 14, which is configured and dimensioned to be inserted into a cannula, handle assembly 12 and fastener removing assembly 20. Handle assembly 12 is positioned at the proximal end of endoscopic portion 14 and functions to actuate the fastener removing assembly 20, which is positioned at the distal end of endoscopic portion 14. The fastener removing assembly 20 of this embodiment has a stationary member, which functions to press against and deform the backspan of a fastener, and a movable member having parallel spaced apart forks, which functions to engage the backspan of a fastener and force the backspan against the stationary member.

FIGS. 2 and 3 illustrate fastener removing assembly 20 and its relationship with endoscopic portion 14. Endoscopic portion 14 includes outer tube 16 and inner rod 18 slidably disposed therein. Inner rod 18 includes distal notch 104, central axial groove 106, and proximal axial groove 108. Nose piece 15 is positioned at a distal end of outer tube 16, with extension 100 sitting within distal opening 17 of outer tube 16.

Figure 6:
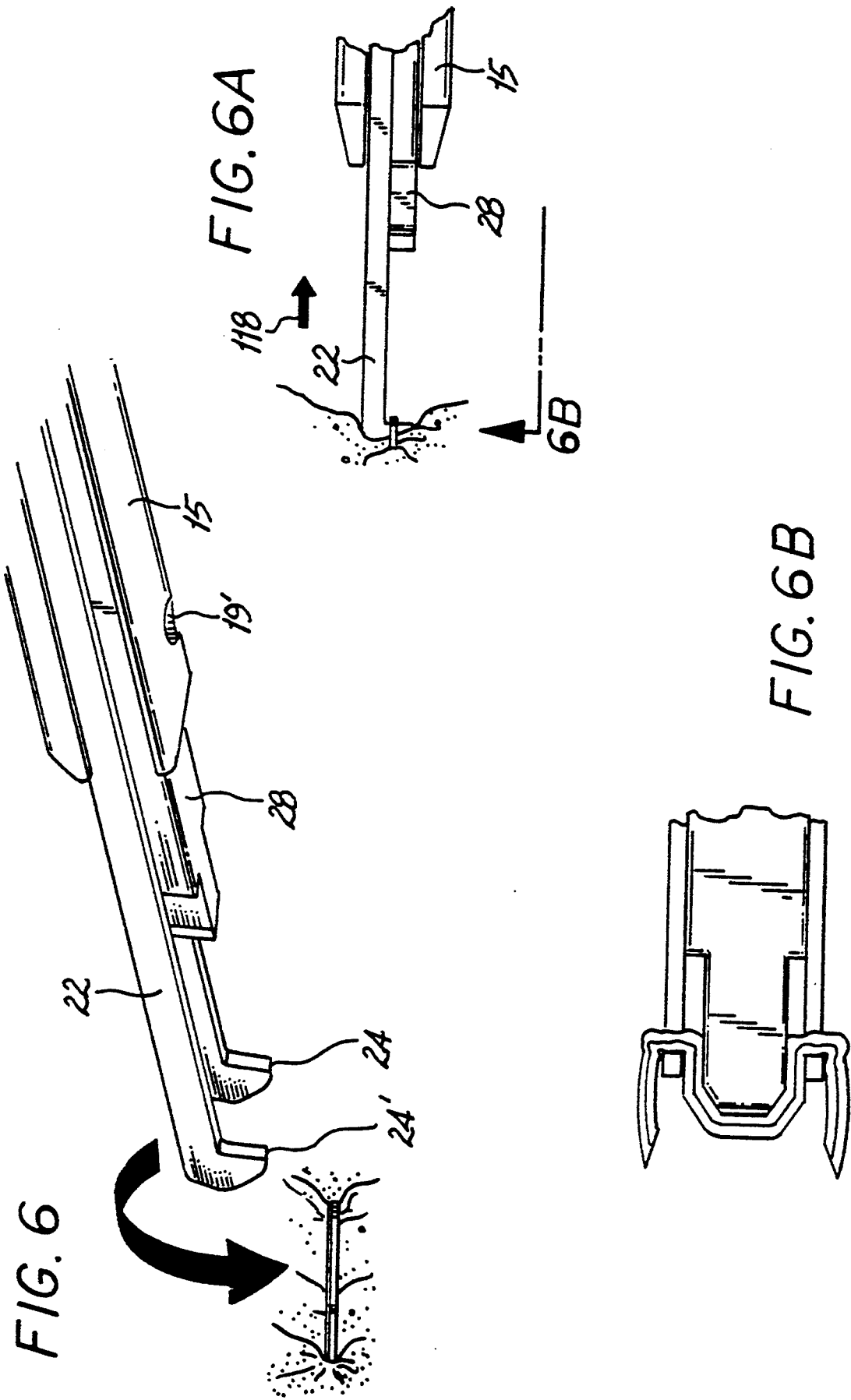
FIG. 6 illustrates the apparatus approaching a fastener to be removed from the body.

With reference to FIGS. 2, 2A and 3, fastener removing assembly 20 includes slidable channel 22 and stationary member 28 positioned therein, both of which are attached to nose piece 15 via pin 25. Pin 25 extends through openings 19 and 19' in the distal end of nose piece 15, through opening 110 in stationary member 28, and through elongated slot 23 in slidable channel 22. Elongated slot 23 allows for sliding movement of channel 22, which will be described below. Notch 104 of inner rod 18 engages the proximal end of channel 22 at aperture 102 such that the two pieces are in axial sliding relationship (e.g., along a longitudinal axis) within nose piece 15. Channel 22 has parallel spaced apart forks 24 and 24' positioned at its distal end and at an angle to the longitudinal axis of channel 22 for purposes of engaging and grasping a fastener to be removed (see also FIGS. 6 and 6A).

FIGS. 3A and 3B illustrate alternative embodiments of forks for engaging the fasteners. Forks 26 and 26' in FIG. 3A are rectangular in shape and have an increased surface area. Forks 27 and 27' in FIG. 3B are essentially trapezoidal. Fork transverse bar 112 is disposed between the parallel forked pairs and has barbs 29 and 29' disposed thereon. The configurations of the forks may be modified to control the manner in which the fastener distorts during removal or to meet specific fastener requirements.

Handle assembly 12 (FIGS. 4 and 5) includes distal stationary handle 30, proximal pivotable handle 32 and latching mechanism 54. Stationary handle 30 and pivotable handle 32 are connected by pivot pin 34 and biased apart by handle spring 38. Inner rod 18 is connected to pivotable handle 32 by pin 33 which engages groove 108 formed in the inner rod. Handles 30 and 32 are shown with finger loops, 35 and 36 respectively, which facilitate grasping by the surgeon.

Latching mechanism 54 is disposed within handle bore 46 and has a latch button 48, which is upwardly or perpendicularly biased by spring 50. Inner rod 18 passes through latch button 48 at orifice 44 (FIG. 4A). Orifice 44 in latch button 48 includes U-shaped protrusion 114 which is configured and dimensioned to engage axial groove 106 of inner rod 18, the movement of which is described below.

Rotating collar 42 is fixedly secured around outer tube 16 and functions to enable a surgeon to rotate endoscopic portion 14 and distal fastener removing assembly 20 to align the removing assembly with the base of a fastener.

In operation, endoscopic portion 14 and fastener removing assembly 20 are inserted into the body through a cannula, which is well known in the art. The surgeon can then rotate collar 42 to cause outer tube 16, inner rod 18 and, consequently, fastener removing assembly 20, to orient forks 24 and 24' to the desired position for engagement of the fastener to be removed. The surgeon positions forks 24 and 24' on the fastener, (see FIG. 6A) and moves proximal pivotable handle 32 distally from a first open position to a second closed position (see FIG. 4, arrow 116) to actuate fastener removing assembly 20. More specifically, this movement of handle 32 causes inner rod 18 to slide proximally further causing attached channel 22 to slide in the same direction (see FIG. 4, arrow 118). The proximal movement of channel 22 causes the fastener to move proximally and become wedged between forks 24 and 24' and stationary member 28. Further proximal movement of channel 22 causes the fastener backspan to distort against stationary member 28 which causes the fastener legs to bend outward, resulting in the fastener distorting to a configuration suitable for removal as shown in FIG. 6B. When inner rod 18 has moved a sufficient distance proximally, such that axial groove 106 is in alignment with opening 44 of latch button 48, spring 50 will force latch button 48 upwardly in the direction of arrow 120. Protrusion 114 will engage axial groove 106, and thereby secure inner rod 18 in a locked position. Thus, movement of inner rod 18 is prevented, which further prevents movement of forks 24, 24', reducing the likelihood that a removed fastener will slip from the apparatus and fall into the body cavity.

The apparatus may then be returned to its unactuated position (i.e., handles open) as shown in FIG. 5, by depressing latch button 48 of latching mechanism 54 in the direction of arrow 122. Such depression of latch button 48 causes protrusion 114 to disengage from axial groove 106 to release inner rod 18. Once inner rod 18 is released, handle return spring 38 will move pivotable handle 32 proximally into its open position (see arrow 124), thereby allowing inner rod 18 and channel 22 to move distally (arrow 126) to their initial position.

Figure 7:
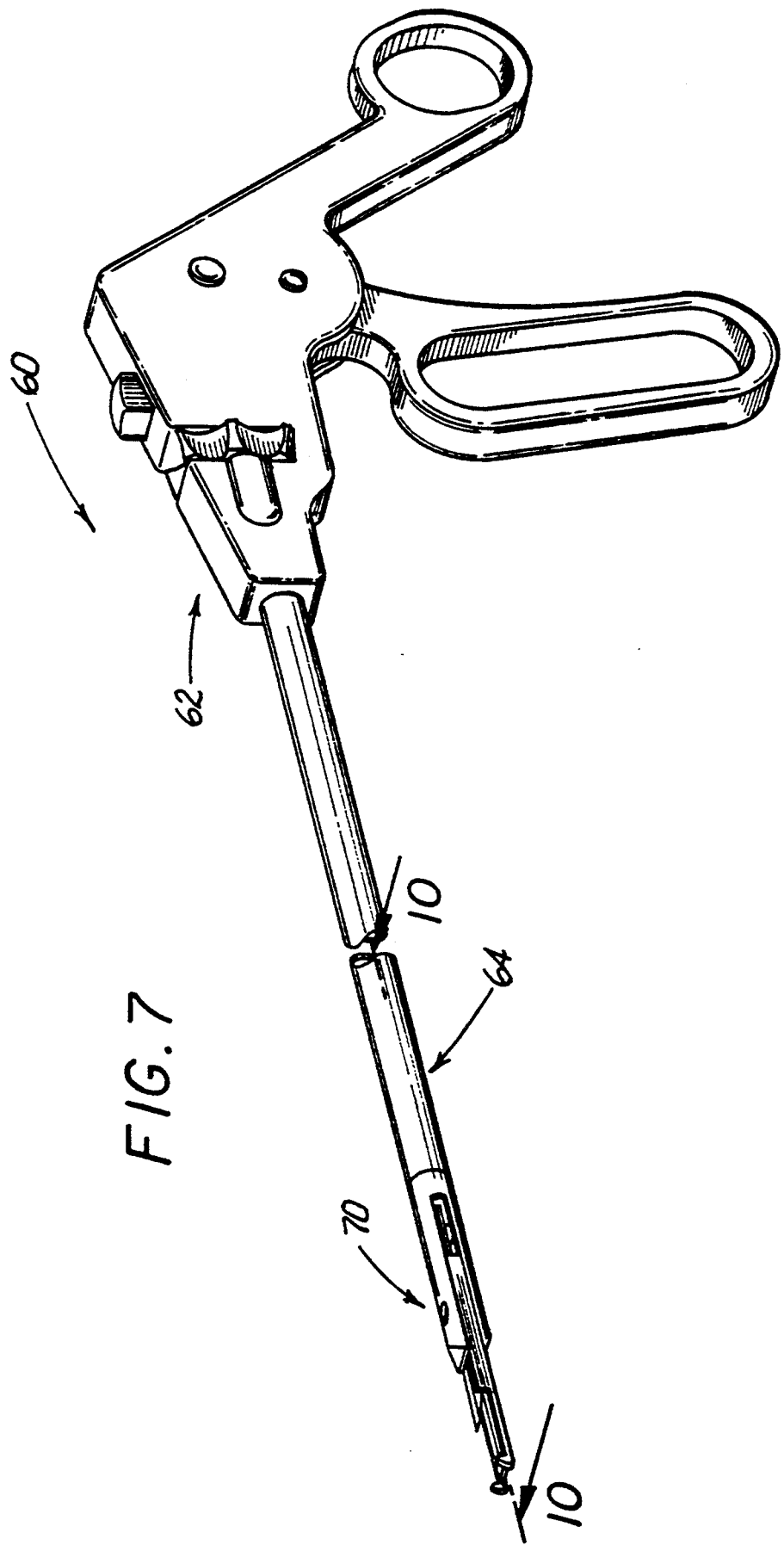
FIG. 7 illustrates a perspective view of a second embodiment of an endoscopic or laparoscopic surgical apparatus of the present invention.

FIG. 7 illustrates an alternative embodiment of the endoscopic or laparoscopic surgical apparatus. Surgical fastener remover 60 comprises endoscopic portion 64, which is configured and dimensioned to be inserted into a cannula, assembly 62 and fastener removing assembly 70. Handle assembly 62 is positioned at the proximal end of endoscopic portion 64 and functions to actuate the fastener removing assembly 70, which is positioned at the distal end of endoscopic portion 64. The fastener removing assembly 70 of this embodiment has a movable member, which functions to press against and deform the backspan of a fastener, and a stationary member having parallel spaced apart forks, which functions to engage and hold the backspan of a fastener while the moveable member presses on the backspan.

Figure 10:
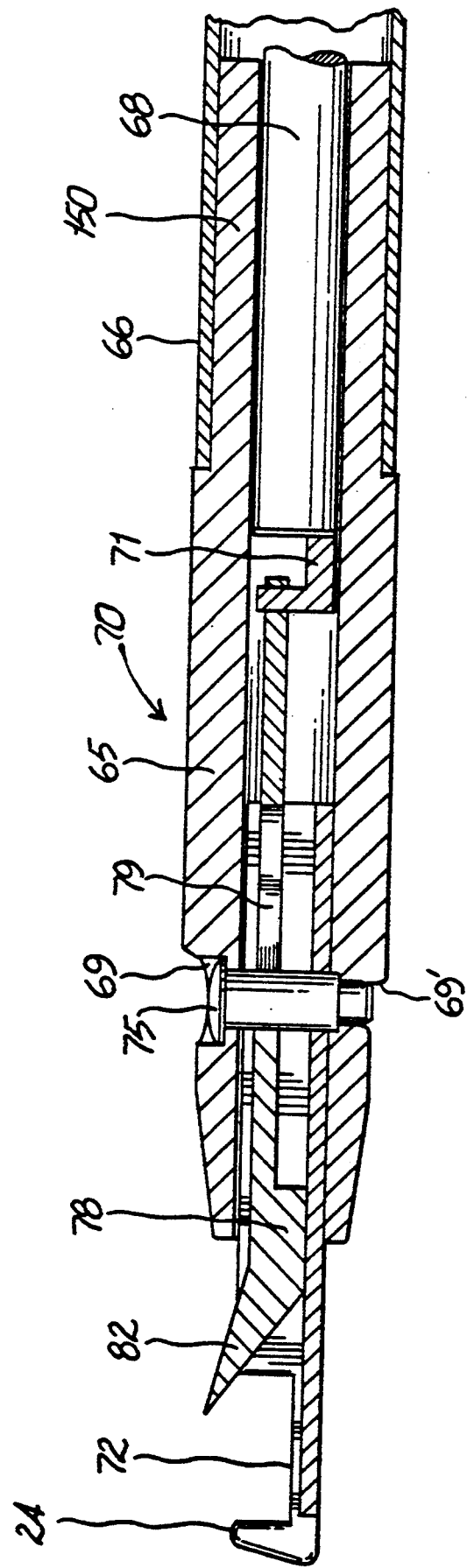
FIG. 10 illustrates a cross sectional view taken along lines 10—10 of FIG. 7.

FIG. 10 illustrates fastener removing assembly 70 and its relationship with endoscopic portion 64. Endoscopic portion 64 includes outer tube 66 and inner rod 68 slidably disposed therein. Nose piece 65 is positioned at a distal end of outer tube 66 with extension 150 sitting within the distal opening of outer tube 66.

Turning now to the fastener removing assembly, 70, illustrated in FIG. 10, the assembly includes stationary channel 72 and moveable member 78 positioned therein, both of which are attached nose piece 65 via pin 75. Pin 75 extends through openings 69 and 69' in the distal end of nose piece 75, through an elongated opening in moveable member 78, and through an opening in stationary channel 72. Elongated slot 79 in moveable member 78 allows for the member to slide within stationary channel 72. Inner rod 68 is secured to the proximal end of moveable member 78 via L-shaped extension 71 so that the two pieces are in axial sliding relationship within nose piece 65.

Movable member 78 preferably includes raised head 82, which functions to depress tissue and enhance exposure of the fastener. Channel 72 is similar to channel 22 of the previous embodiment in that it has parallel spaced apart forks. The forks may likewise have various configurations, such as those shown in FIGS. 3A and 3B.

Figure 8:
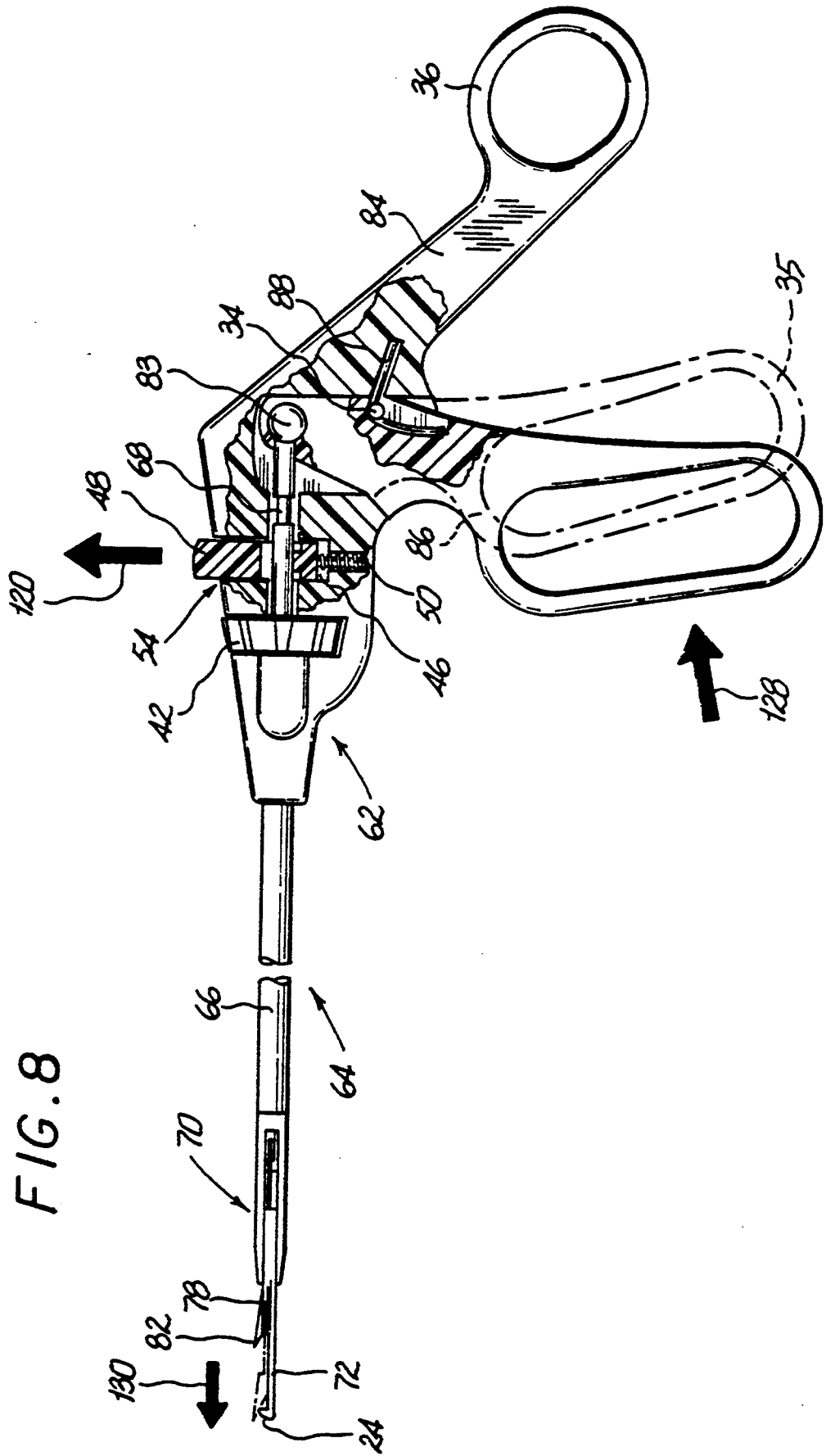
FIG. 8 illustrates a side plan of the apparatus of FIG. 7 showing a portion of the handle assembly cut away and depicting the movement of the pivotable handle from the open to the closed position.
Figure 9:
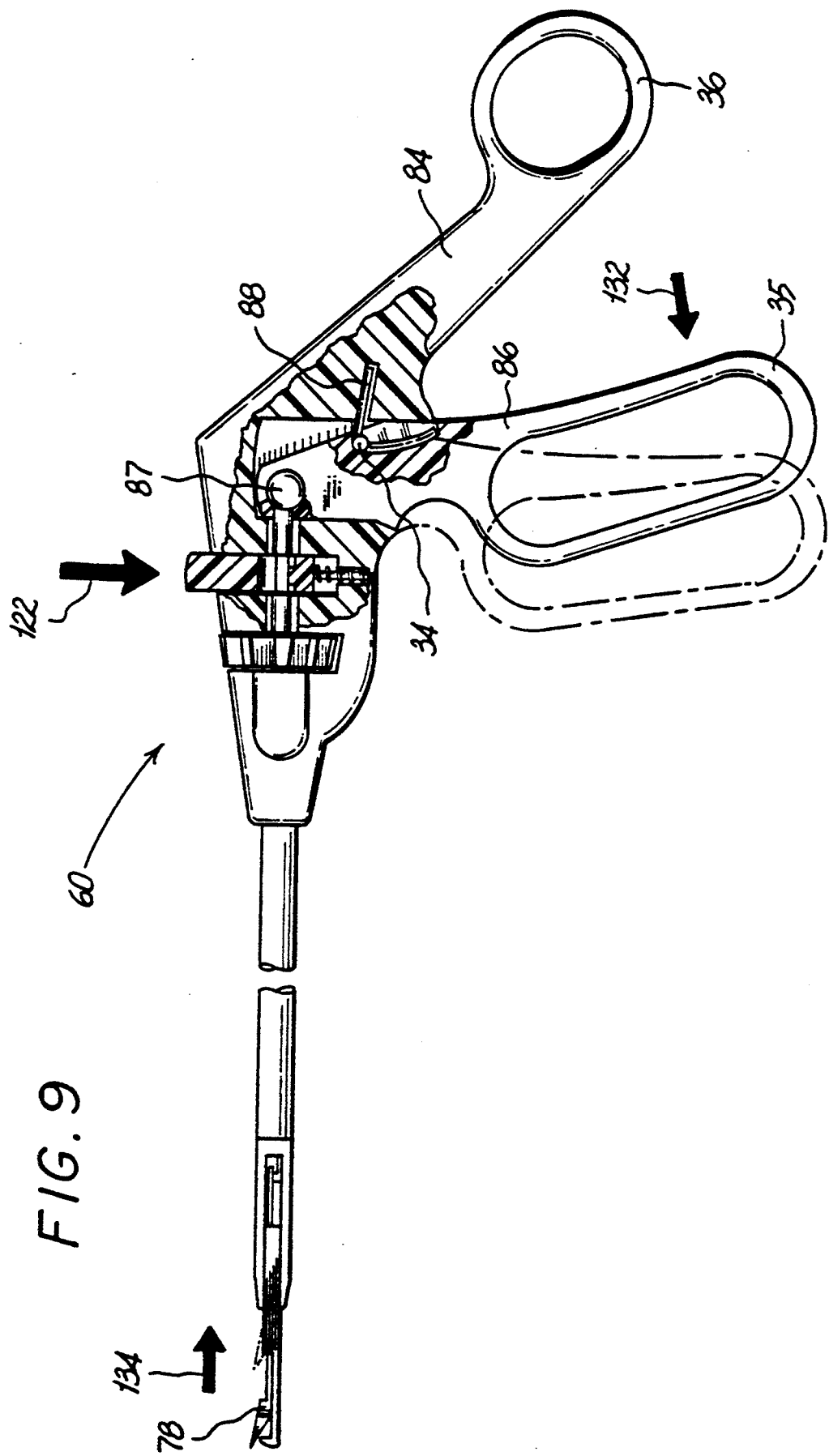
FIG. 9 illustrates the apparatus of FIG. 8, depicting the movement of the pivotable handle from the closed to the open position.

The handle assembly 62 of the apparatus includes proximal stationary handle 84, distal pivotable handle 86 and latching mechanism 54 as best shown in FIGS. 8 and 9. Handles 84 and 86 are shown with finger loops, 36 and 35 respectively, to facilitate grasping by the surgeon. Stationary handle 84 and pivotable handle 86 are connected by pivot pin 34 and biased apart by handle spring 88. Inner rod 68 is connected at its proximal end to pivotable handle 86 by inner rod pin 83. Latching mechanism 54 is disposed within handle bore 46 and has a latch button 48 which is upwardly biased by spring 50. Inner rod 68 interacts with latch button 48 in the same manner as the previous embodiment.

In operation, endoscopic portion 64 and fastener removing assembly 70 are inserted into the body through a cannula. The surgeon can then rotate collar 42 to position the fastener removing assembly in the desired position, and then the forks are placed in engagement with the fastener. As illustrated in FIG. 8, fastener removing assembly 70 may then be actuated by moving distal pivotable handle 86 proximally from a first position to a second position (see arrow 128). This movement of handle 86 causes inner rod 68 to slide distally causing attached movable member 78 to slide in the same direction (see arrow 130). Distal movement of movable member 78 causes the fastener to become wedged between moveable member 78 and forks 24,24' on stationary channel 72. Further distal movement of movable member 78 causes the fastener backspan to distort between the forks which causes the fastener legs to bend outward, resulting in the fastener distorting to a configuration suitable for removal as shown in FIG. 6B. When inner rod 68 has moved a sufficient distance distally, spring 50 will force latch 48 upwardly (see arrow 120) to lock inner rod 68 in a fixed position, in a manner similar to that described in the previous embodiment.

The apparatus may then be returned to its unactuated position (i.e., handles open) by depressing latch button 48 (see arrow 122 of FIG. 9). Once inner rod 68 is released, handle spring 88 will force pivotable handle 86 distally (arrow 132) into the first position thereby allowing inner rod 68 and movable member 78 to move proximally (arrow 134) to their initial position.

While the invention has been particularly shown and described with reference to the preferred embodiments, it will be understood by those skilled in the art that various modifications in form and detail may be made therein without departing from the scope and spirit of the invention. Accordingly, such modifications are to be considered within the scope of the invention as defined by the claims.

What is claimed is:

1. A surgical apparatus for removing from the body a fastener having a pair of legs joined by a backspan having top and bottom portions, the apparatus comprising:
   a) an endoscopic portion;
   b) means positioned at a distal end of said endoscopic portion for removing the fastener, said fastener removing means comprising a stationary member and a movable member, wherein said movable member comprises parallel spaced apart fork means for engaging said backspan; and
   c) means remote from said distal end of said endoscopic portion for actuating said fastener removing means;
   wherein said movable member engages the fastener backspan bottom portion and proximal movement of said movable member moves said fastener proximally to cause said fastener backspan top portion to press against said stationary member further causing said fastener to deform to a configuration suitable for removal.

2. A surgical apparatus for removing from the body a fastener having a pair of legs joined by a backspan having top and bottom portions, the apparatus comprising:
   a) an endoscopic portion;
   b) means positioned at a distal end of said endoscopic portion for removing the fastener, said fastener removing means comprising a stationary member and a movable member, wherein said stationary member comprises parallel spaced apart fork means for engaging said backspan; and
   c) means remote from said distal end of said endoscopic portion for actuating said fastener removing means;
   wherein said stationary member engages the fastener backspan bottom portion and distal movement of said movable member causes said movable member to press against said fastener backspan top portion further causing said fastener to deform to a configuration suitable for removal.

3. A surgical apparatus according to claim 2 wherein said fastener removing actuating means comprises a handle assembly having at least one pivotable handle.

4. A surgical apparatus for removing from the body a fastener having a pair of legs joined by a backspan, the apparatus comprising:
   a) an endoscopic portion;
   b) means positioned at a distal end of said endoscopic portion for removing the fastener, said fastener removing means comprising a stationary member and a movable member, wherein said movable member moves longitudinally along a longitudinal axis of said endoscopic portion and wherein one of said members comprises parallel spaced apart forks; and
   c) means remote from said distal end of said endoscopic portion for actuating said fastener removing means.

5. A surgical apparatus according to claim 4 wherein said endoscopic portion is rotatable relative to said handle assembly.

6. A surgical apparatus according to claim 5 wherein said handle assembly comprises means for rotatably moving said endoscopic portion.

7. A surgical apparatus according to claim 6 wherein said means for rotatably moving said endoscopic portion comprises a collar positioned around the outer tube of said endoscopic portion.

8. A surgical apparatus for removing from the body a fastener having a pair of legs joined by a backspan, the apparatus comprising:
   a) an endoscopic portion comprising an outer tube and an inner rod slidably disposed therein;
   b) means positioned at a distal end of said endoscopic portion for removing a fastener, said fastener removing means comprising parallel spaced apart forks; and
   c) means remote from said distal end of said endoscopic portion for actuating said fastener removing means, said actuating means comprising a handle assembly having at least one pivotable handle and wherein said inner rod is secured to said at least one pivotable handle.

9. A surgical apparatus according to claim 8 wherein said at least one pivotable handle is movable from a first position to a second position and further comprising means for retaining said at least one pivotable handle is said second position.

10. A surgical apparatus according to claim 9 wherein said means for retaining said at least one pivoting handle comprises a latching member disposed within a bore in said handle assembly and said latching member retaining said inner rod in a locked position.

11. A surgical apparatus according to claim 10 wherein said latching member comprises an orifice through which said inner rod passes and a protrusion disposed within said orifice which is configured and dimensioned to engage an axial groove in said inner rod.

12. A surgical apparatus according to claim 10 comprising means for releasing said latching member.

13. A surgical apparatus according to claim 8 wherein said fastener removing means further comprises a stationary member and a movable member.

14. A surgical apparatus according to claim 13 wherein said forks are movable and cooperate with said inner rod of said endoscopic portion.

15. A surgical apparatus according to claim 14 wherein said parallel spaced apart forks engage the backspan of said fastener and proximal movement of said forks causes proximal movement of said fastener causing said backspan to press against said stationary member further causing said fastener to deform to a configuration suitable for removal.

16. A surgical apparatus according to claim 13 wherein said parallel spaced apart forks are stationary and engage the backspan of said fastener and distal movement of said movable member causes said movable member to press against said backspan further causing said fastener to deform to a configuration suitable for removal.

17. A surgical apparatus configured and dimensioned for insertion through a cannula comprising:
   a) an endoscopic portion comprising an outer tube and an inner rod slidably disposed therein;
   b) tool means positioned at a distal end of said endoscopic portion, said inner rod cooperating with said tool means;
   c) means remote from a distal end of said endoscopic portion for manipulating said inner rod; and
   d) means for locking said inner rod in a fixed position, said locking means comprising a latching member slidable in a direction substantially perpendicular to said endoscopic portion and engaging said inner rod.

18. A surgical apparatus according to claim 17 wherein said latching member is positioned within a bore in said manipulating means and comprises an orifice through which said inner rod passes.

19. A surgical apparatus according to claim 18 wherein said latching member further comprises a protrusion which is configured and dimensioned to engage an axial grove in said inner rod.

20. A surgical apparatus according to claim 19 comprising means for releasing said latching member.

21. A surgical apparatus according to claim 17 wherein said latching member is spring biased upwardly.

22. A surgical apparatus according to claim 17 wherein said tool means comprises means for removing from the body a fastener having a pair of legs joined by a backspan.

23. A surgical apparatus for removing from the body a fastener having a pair of legs joined by a backspan, the apparatus comprising:
   a) an endoscopic portion;
   b) means positioned at a distal end of said endoscopic portion for removing the fastener, said fastener removing means comprising a stationary member and a movable member, wherein said movable member moves longitudinally along a longitudinal axis of said endoscopic portion;
   c) actuating means positioned at a proximal end of said endoscopic portion for actuating said fastener removing means; and locking means disposed in said actuating means for locking said movable member in a fixed position.

24. A surgical apparatus according to claim 23 wherein said movable member comprises parallel spaced apart forks.

25. A surgical apparatus according to claim 23 wherein said stationary member comprises parallel spaced apart forks.

26. A surgical apparatus according to claim 23 wherein said actuating means comprises a handle assembly.

* * * * *